(12) United States Patent
Kallick

(10) Patent No.: US 7,820,405 B2
(45) Date of Patent: Oct. 26, 2010

(54) SPECIFIC BACTERIAL INCLUSIONS IN BONE MARROW CELLS INDICATE SYSTEMATIC LUPUS ERTHEMATOSUS, AND TREATMENT FOR LUPUS

(75) Inventor: Charles A. Kallick, Lemont, IL (US)

(73) Assignee: Sphingomanas Research Partners, L.P., Lemont, IL (US)

( * ) Notice: Subject to any disclaimer, the term of this patent is extended or adjusted under 35 U.S.C. 154(b) by 129 days.

(21) Appl. No.: 11/461,900

(22) Filed: Aug. 2, 2006

(65) Prior Publication Data

US 2007/0031820 A1 Feb. 8, 2007

Related U.S. Application Data

(60) Provisional application No. 60/706,125, filed on Aug. 5, 2005.

(51) Int. Cl.
*C12Q 1/04* (2006.01)
*C12Q 1/02* (2006.01)
*C12Q 1/00* (2006.01)

(52) U.S. Cl. .................. 435/34; 435/29; 435/4
(58) Field of Classification Search ................. None
See application file for complete search history.

(56) References Cited

U.S. PATENT DOCUMENTS 5,795,563 A * 8/1998 Kallick ............... 424/9.361
2005/0042688 A1 * 2/2005 Hashemi ................ 435/7.2

\* cited by examiner

*Primary Examiner*—Jon P Weber
*Assistant Examiner*—Laura Schuberg
(74) *Attorney, Agent, or Firm*—Husch Blackwell Welsh & Katz

(57) ABSTRACT

A method for diagnosing for the presence of systemic lupus erythematosus (SLE) in a patient is disclosed. In accordance with this method, megakaryocytes present in bone marrow of a person suspected of having SLE are assayed for the presence of internal bacterial structures that specifically stain with an intercalating dye. The presence of those specifically stainable structures within the patient's megakaryocytes indicates that the patient has SLE. Treatment of an SLE patient with an antibiotic is contemplated. Treatment of a patient that has SLE comprises administering to that patient (i) an antibacterial amount of a rifamycin along with an antibacterial amount of a macrolide, (ii) an antibacterial amount of a tetracycline, or (iii) an antibacterial amount of a quinolone, or a mixture of two or more of i, ii and iii. The treatment is continued until the patient's megakaryocytes no longer contain specifically stainable structures, and until no further evidence of infection is present.

13 Claims, 5 Drawing Sheets

SPECIFIC BACTERIAL INCLUSIONS IN BONE MARROW CELLS INDICATE SYSTEMATIC LUPUS ERTHEMATOSUS, AND TREATMENT FOR LUPUS

CROSS-REFERENCE TO RELATED APPLICATION

This application claims benefit of provisional application Ser. No. 60/706,125 that was filed on Aug. 5, 2005.

TECHNICAL FIELD

This invention relates to the diagnosis of systemic lupus erythematosus in a human patient. More particularly, this invention relates to an assay for the presence of specific bacterial inclusions within human bone marrow cells that indicates that the patient has systemic lupus erythematosus (SLE), and treatment to lessen or eliminate the load of the bacterium.

BACKGROUND ART

Systemic lupus erythematosus (SLE) is severe disease characterized by chronic inflammation (swelling, redness, and pain). Patients having this disease produce antibodies that target cells of their own body tissues. The antibody-targeted cells are then destroyed by white blood cells in the body causing cell death that leads to inflammation. As such, SLE is known as an autoimmune disease. Crow et al., "Etiologic Hypothesis for Systemic Lupus Erythematosus," in LaHita, *Systemic Lupus Erythematosus*, Churchill, Livingston, N.Y. (1987) page 51 ff. SLE affects many body systems including skin, joints, blood, lungs, kidneys, heart, brain, gastrointestinal tract, bone marrow, liver, and nervous tract. Crow et al., "Etiologic Hypothesis for Systemic Lupus Erythematosus," in LaHita, *Systemic Lupus Erythematosus*, Churchill, Livingston, N.Y. (1987) page 51 ff.

The present diagnosis for SLE is an art form practiced by rheumatologists or other physicians. In one form, the practitioner seeks eleven indicia: malar rash, discoid rash, oral ulcers, arthritis, serositis, renal disorder, neurologic disorder, hematologist disorder, immunologic disorder and anti-nuclear antibodies (ANA). SLE is presumed if four of the eleven are present. LaHita, *Lupus Erythematosus*, 2nd. ed., Churchill, Livingston, N.Y. (1992) pages 372-373. Other assays that can be and are used to diagnose the presence of SLE in a patient include separate assays for ANA, complement levels, the presence of rheumatoid factor, hyperglobulinemia, false positive syphilis test, LE cell test, anti-DNA antibodies, anti-SMP antibodies, anti-RMP antibodies, anti-Smith antibodies, anemia, leucopenia, thrombocytopenia, positive direct Coombs' test, and anti-double-stranded DNA (anti-dsDNA) antibodies. LaHita, *Lupus Erythematosus*, 2nd. ed., Churchill, Livingston, N.Y. (1992). As is seen, none of these assays is definitive for the disease.

Although there is marked similarity to an infectious entity, an exhaustive search for an etiologic agent has not until recently yielded any candidates that fulfill the criteria for causation of this disease until now. Crow et al., "Etiologic Hypothesis for Systemic Lupus Erythematosus," in Lahita *Systemic Lupus Erythematosus*, Churchill, Livingston, N.Y. (1987) page 51 ff; Pincus, *Arthr. & Rheum.*, 20:149-158 (1982). More recently, the consideration of bacteria and *mycoplasmas* with unique capacities to perturb immune systems has led to new hypotheses in regard to the infectious trigger of SLE.

For example, intra-erythrocyte organisms with characteristics that were thought to be Haemobartonella-like were first suggested as exogenous agents in SLE by Kallick et al., *Nature New Biology*, 236:145-146 (1972). That report was further developed by a later report of antigenic similarities between SLE or lupus nephritis and diseases caused by *Anaplasma marginale*, an intra-erythrocytic parasite of cattle, and a member of the family Anaplasmataceae. Kallick et al., *Arthr. Rheum.*, 23:197-205 (1980).

Further, exogenous intra-erythrocytic structures seen in the same erythrocyte by Giemsa or acridine orange staining and phase contrast microscopy have been observed in most patients with SLE, and are illustrated in U.S. Pat. Nos. 5,972,309 and 5,795,563. These stained structures are identical or similar in appearance to *Mycoplasma haemofelis*, the causative agent of feline infectious anemia, as discussed below.

A specific group of *Mycoplasmas* recognized as Haemoplasmas also produce hematological disease in cats, dogs, mice, and swine. They exhibit latency and chronicity as well as an acute syndrome and intermittent infection of the erythrocytes and can be seen in the acute phase of early infection, although not easily in the chronic phase. They have not been reproducibly cultured or transmitted to other than related animal species.

The locus of infection of the erythrocyte in the Haemoplasmas, *M. haemocanis, M. haemofelis,* and *M. haemosuis* is seen on the surface of the erythrocytes, though in mice, *M. haemomuris* also known as *Haemobartonella muris*, is within the erythrocyte. Early descriptions of these agents were mediated by the observed position of the parasite on the erythrocyte.

In animal disease, antibiotics control hemolytic anemia, the primary pathologic event, only if given early in the course of the illness. Late in the course of animal illness, the hemolytic anemia is mediated by antibody formation and antibiotics do not appear to affect the course. In veterinary literature, one antibiotic that appears to suppress some of the clinical manifestations is tetracycline and analogues. Franklin et al., *Southwestern Vet.*, 15:131-139 (1962).

Several humans with SLE or connective tissue disease have been treated with tetracycline (doxycycline) in preliminary work of the inventor based on the presumption of Anaplasmataceae parasitemia. Wanduragala et al. in, *Rickettsial and Chlamydial Diseases of Domestic Animals*, Waldehewit ed., Pergamon Press, Oxford, (1993) page 79.

Aureomycin, a tetracycline-like drug, had been proposed as a treatment in the 1940s for rheumatoid diseases with claims of some degree of success. [Brown et al., *J. Lab. Clin. Med.*, 34:1404-1410 (1949); Scheff et al., *Infec. Dis.*, 98:113 (1956).] These phenomena suggest that the tetracycline drugs are of benefit in the syndrome of SLE.

Current SLE therapy relies upon heavy steroid use concurrent with immunosuppressives and/or plasmaphoresis. It is of interest that infections in animals by bacteria then called Anaplasmataceae, are almost uniquely among infectious diseases, ameliorated by steroids. [Scheff et al., *Infec. Dis.*, 98:113 (1956); Ristic et al., *J. Vet. Res.*, 19:37 (1958)]

No presently used therapy is completely satisfactory. Although the life expectancy of *lupus* patients has been considerably increased, the ravages of therapeutic side effects and the constant fatigue take a severe toll. Dubois, *Lupus Erythematosus*, 2d ed., U.S. California Press, Los Angeles (1974).

It would therefore be beneficial if a more definitive diagnosis of SLE patients could be found, and if the patients so identified could be more effectively treated. The description that follows describes a diagnostic method that is believed to be definitive for SLE, and a treatment regimen that deals with the causative agent in SLE and can eliminate that agent from a patient's body.

BRIEF SUMMARY OF THE INVENTION

One aspect of this invention contemplates a diagnostic method for determining the presence of systemic *lupus erythematosus* (SLE) in a patient. The diagnostic method comprises assaying megakaryocytes present in bone marrow of a person suspected of having SLE for the presence of specific bacterial structures within those cells. Those internal bacterial structures specifically stain with a dye such as a DNA intercalating dye like Giemsa, ethidium bromide, acridine orange, or the like as are well known in the art. The presence of those specifically stainable structures within the patient's megakaryocytes indicates that the patient has SLE.

The present invention also contemplates a process for treating a person whose megakaryocytes contain intercalating dye-stainable bacterial structures. The process comprises administering to such a patient an antibiotic agent or a mixture thereof. More particularly, that treatment comprises administering to that patient (i) an antibacterial amount of a rifamycin along with an antibacterial amount of a macrolide, (ii) an antibacterial amount of a tetracycline, or (iii) an antibacterial amount of a quinolone, or a mixture of two or more of i, ii, and iii. Preferably, the antibiotic mixture comprises rifamycin and clarithromycin, or doxycycline.

The present invention has several benefits and advantages. One benefit is that it provides a process for treating a patient with SLE to lessen or remove the etiological bacteria from the bone marrow of an SLE patient.

An advantage of the invention is that its process of treatment can be carried out with an antibacterial agent whose safety in humans has already been demonstrated.

Another benefit of the invention is that its assay provides a definitive diagnosis as compared to a differential diagnosis as is currently the case.

Still further benefits and advantages of the present invention will be apparent to a skilled worker from the description that follows.

BRIEF DESCRIPTION OF THE DRAWINGS

In the drawings forming a part of this invention.

DETAILED DESCRIPTION OF THE INVENTION

The present invention contemplates a method for diagnosis of systemic lupus erythematosus in a human. In accordance with this method, megakaryocytes present in bone marrow of a person suspected of having SLE are assayed for the presence of internal bacterial structures that specifically stain with a DNA intercalating dye. The presence of those specifically stainable structures within the patient's megakaryocytes indicates that the patient has SLE. Preferably, the dye is Giemsa, ethidium bromide or acridine orange.

Figure 5:
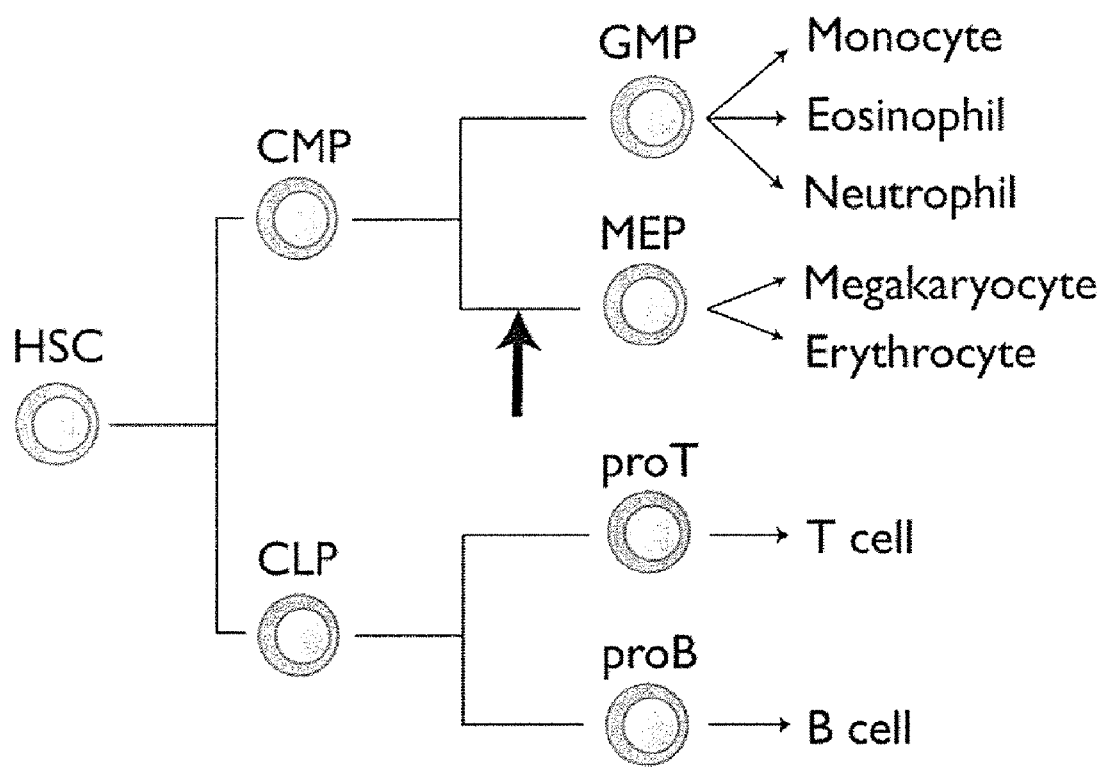
FIG. 5, from Iwasaki et al., *Immunology*, 19:451-462 (2003), is a schematic depiction of hematopoietic cell differentiation in which HSC=Human Stem Cell, CMP=myelomocytic progenitor, CLP=Lymphoid progenitor, GMP=granulocyte-monocyte progenitor, MEP=erythrocyte-megakaryocyte progenitor, and ProT=Lymphocyte T cell progenitor, and ProB=lymphocyte B cell progenitor.

As noted previously, stainable exogenous intra-erythrocytic bacterial structures have been documented in patients with SLE. The diagram of FIG. 5 illustrates that erythrocytes arise from differentiation of erythrocyte-megakaryocyte progenitor (MEP) cells. In view of the findings reported herein that megakaryocytes of SLE patients contain stainable exogenous bacterial structures that are indistinguishable from the similar structures found in erythrocytes, it appears as though the progenitor megakaryocytic cells are a situs of infection with the erythrocytes obtaining their infection from parental cells prior to differentiation, rather than after differentiation.

The present invention also contemplates treatment of a patient whose megakaryocytes contain one or more exogenous bacterial structures that are stainable with a nucleic acid intercalating dye such as acridine orange and with Giemsa, and are also visible with phase contrast microscopy, such as a patient suffering from systemic lupus erythematosus (SLE). That treatment comprises administering to that patient an antibacterial agent that is (i) an antibacterial amount of a rifamycin along with an antibacterial amount of a macrolide, (ii) an antibacterial amount of a tetracycline, or (iii) an antibacterial amount of a quinolone, or a mixture of two or more of i, ii and iii.

SLE patients are often treated with a steroid compound such as prednisone as a palliative. That treatment is maintained during the antibacterial treatment and as long as is required.

Macrolides are hydroxylated macrocyclic lactones having 12 to 20 atoms in the primary ring. Although more than thirty macrolides are known, erythromycin, its analogues and derivatives are most clinically important, and the word macrolide is used herein to mean such compounds. A macrolide can be administered orally or parenterally, and oral administration is preferred.

As used herein, a derivative of erythromycin has a biological activity similar to that of erythromycin itself, and a macrocyclic ring structure and pendant saccharide moieties that are the same as erythromycin, but additionally has one or more erythromycin substituent groups reacted with another moiety to form a functional group different from that present at the same position in erythromycin, such as one or more erythromycin hydroxyls being etherified with a methyl group or esterified with an acetyl or propionyl group in the derivative. Exemplary erythromycin derivatives include clarithromycin (methyl ether), erythromycin 2'-acetate octadecanoate (2'-acetate, stearate salt), erythromycin estolate (2'-propanoate dodecylsulfate salt) and the like. Clarithromycin is particularly preferred. Dirithromycin is a prodrug that is converted to erythromycylamine during intestinal absorption.

An erythromycin analogue is a compound that has a biological activity similar to that of erythromycin itself, a macrocyclic ring structure that is different from erythromycin and contains two atoms more or less in the macrocyclic ring than does erythromycin, while having similar ring substituents to erythromycin or an erythromycin derivative. An exemplary erythromycin analogue is azithromycin. Other similar macrolides include celithromycin and spiramycin.

Clarithromycin is available as BIAXIN™ FILMTAB® tablets from Abbott Laboratories. These commercial tablets each contain 250 mg or 500 mg of clarithromycin. Usual dosages are 250 to about 4000 mg per day in one to four about evenly spaced oral administrations. A daily administration of a total of about 500 to 1000 mg in two to four administrations is preferred with rifampin for synergetic activity.

Clarithromycin can be administered without regard to a patient's stomach contents; i.e., given on a full or empty stomach. On the other hand, the bioavailability of erythromycin is lessened when that drug is administered to a patient who had recently eaten.

It is preferred to co-administer a rifamycin with a macrolide. The phrase "a rifamycin" is meant to include rifamycin itself as well as rifamycin derivatives as are discussed below. Rifamycin is a broad-spectrum antibiotic produced by *Streptomyces mediterranei* that is active against most gram-positive organisms and has variable activity against gram-negative organisms such as *Escherichia coli* and *Pseudomonas*. Rifamycin and its derivatives also have intracellular bactericidal activity.

Rifampin is a particularly preferred rifamycin derivative that is available from Aventis as RIFADIN®, and can administered per orally or by injection in an antibacterial amount. Capsules for oral administration are available that contain 150 or 300 mg of rifampin per capsule. Usual adult oral administrations are 600 mg once per day, usually with water about one hour before a meal, with dosages of about 450 to about 900 mg per day being contemplated. A combination therapeutic sold by Aventis under the name RIFATER can also be used. This drug contains rifampin, isoniazid and pyrazinamide.

Rifabutin, available under the trademark MYCOBUTIN® from Pharmacia-Upjohn, is also a preferred rifamycin derivative. Rifapentine, available from Aventis under the trademark PRIFTIN®, and rifamide are other rifamycin derivatives that can also be used.

It is to be understood that the macrolide and rifampin need not be administered via the above-noted commercially available forms. Rather, those drugs can be compounded into a composition for administration to a SLE patient using well-known pharmaceutical techniques.

Tetracyclines are a family of compounds containing four fused rings that typically include ethylenic unsaturation in one or more of the rings and a plurality of oxygen-containing functional groups bonded to the rings. These compounds became the most prescribed broad-spectrum antibiotic in the United States within three years of their introduction and remain a drug of choice for a number of serious bacterial infections.

Tetracycline was the first therapeutically superior drug to be made by chemical alteration of an antibiotic produced by microbial metabolism. It sparked a wide-scale search for superior structurally modified antibiotics, which has provided most of the important antibiotic discoveries made since then. Illustrative approved tetracycline compounds include tigacycline, doxacycline and minocycline.

Quinolone compounds typically contain two fused 6-membered rings that are aromatic and include a ring nitrogen atom having a keto group directly across the ring. The first quinolone, nalidixic acid, contains two ring nitrogen atoms, is effective against Gram (−) bacteria. Nalidixic acid was first marketed in 1965 and is still available.

Ciprofloxacin (cipro) is a drug within the quinolone class, specifically the fluoroquinolones. It is used to treat bacterial infections in various parts of the body when given orally. In addition to cipro, useful quinolones further include levofloxacin, moxifloxacin, gatifloxacin, tefloxacin and trovafloxacin.

Figure 1:
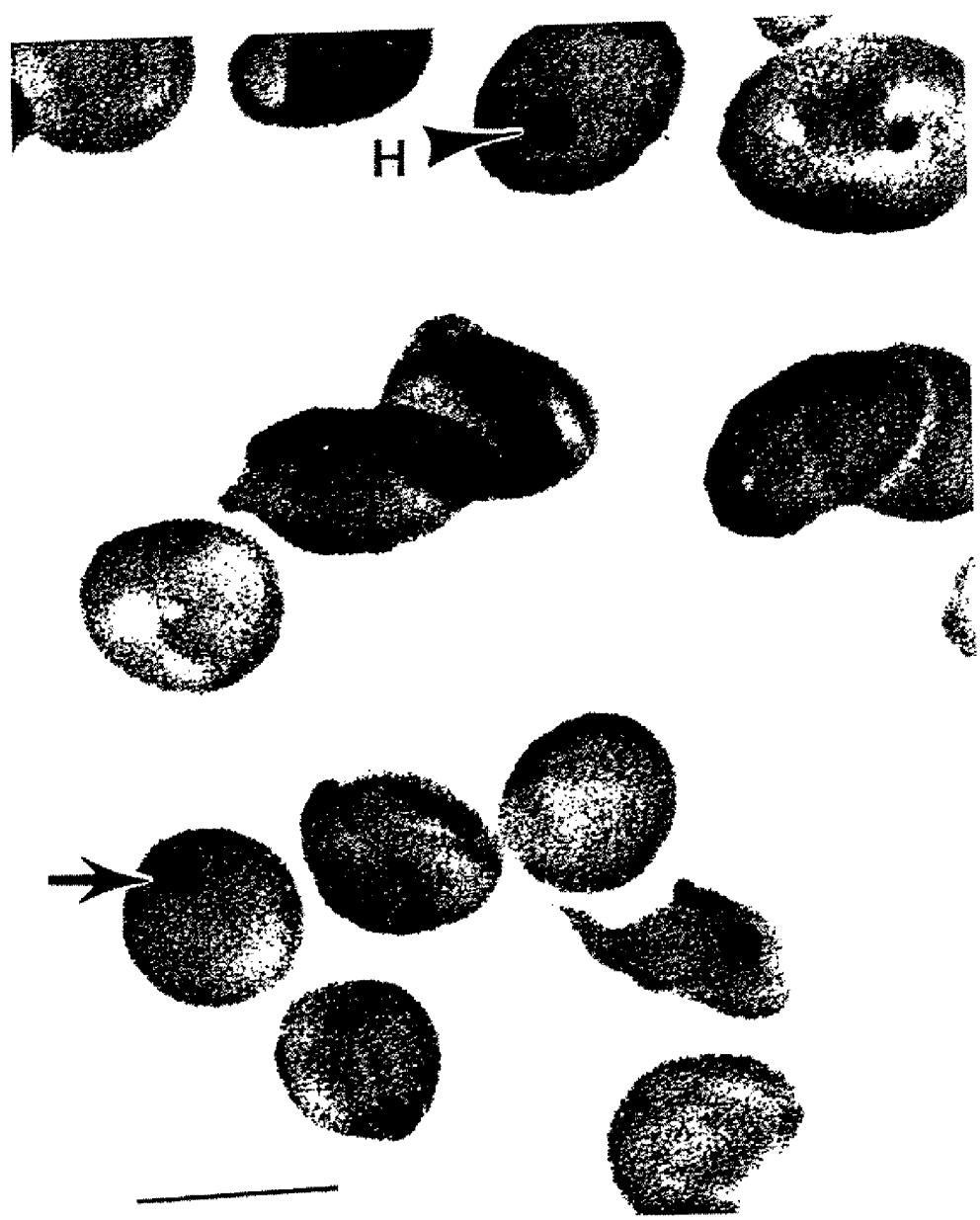
FIG. 1 is taken from the inventor's U.S. Pat. Nos. 5,972,309 and 5,795,563 and shows a thin blood film obtained from a patient of the Examples and stained for one hour with filtered Giemsa stain. This patient was splenectomized and had systemic lupus erythematosus. Several individual erythrocytes are visualized. The stained structure within the erythrocyte indicated by the arrow is the infectious bacterium referred to herein as Mycoplasma haemosapiens. The structure in another erythrocyte designated "H" is a Howell-Jolly body often seen in splenectomized patients. A Howell-Jolly body can be differentiated from the bacterium by size and phase refraction but not by staining characteristics. Original magnification ×630.
Figure 2:
FIG. 2 is the same field of erythrocytes of the patient as seen in FIG. 1 and is also taken from the inventor's U.S. Pat. Nos. 5,972,309 and 5,795,563. The same erythrocytes are visualized, but the optical view is by phase contrast. In this mode, the Giemsa-stained bodies are poorly visualized. Doubly retractile structures occupy the same positions and locations within the erythrocytes of those structures designated as the Mycoplasma haemosapiens, as seen with phase contrast optics. The structure of FIG. 1 designated "H" is absent in the phase contrast view as the Howell-Jolly structure does not contain a retractile body. Original magnification is ×630.
Figure 3:
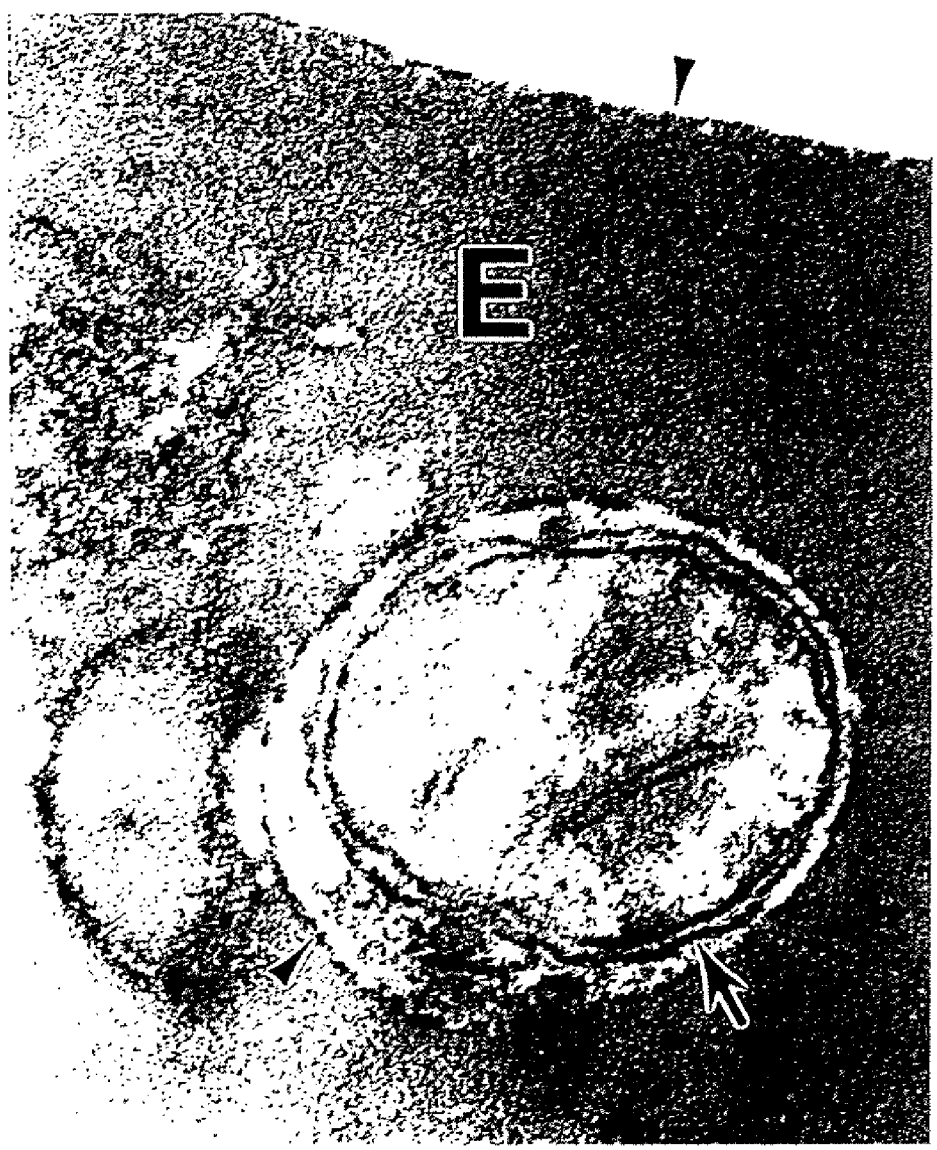
FIG. 3 is an electron micrograph taken from the inventor's U.S. Pat. Nos. 5,972,309 and 5,795,563 and showing a small portion of an erythrocyte from the same patient as in FIGS. 1 and 2. The area designated "E" is the matrix of the erythrocyte. The small arrow above and to the right of the "E" designates the erythrocyte membrane. The large arrow designates the double membrane enclosing the exogenous, infectious bacterium, and appears to have some of the characteristics of a gram-negative bacterial membrane. The limiting membrane of the vacuole layer surrounding the bacterium is designated by the unmarked wedge near the left-hand side of the micrograph, and morphologically resembles erythrocyte membrane. The original magnification ×65,000.
Figure 4:
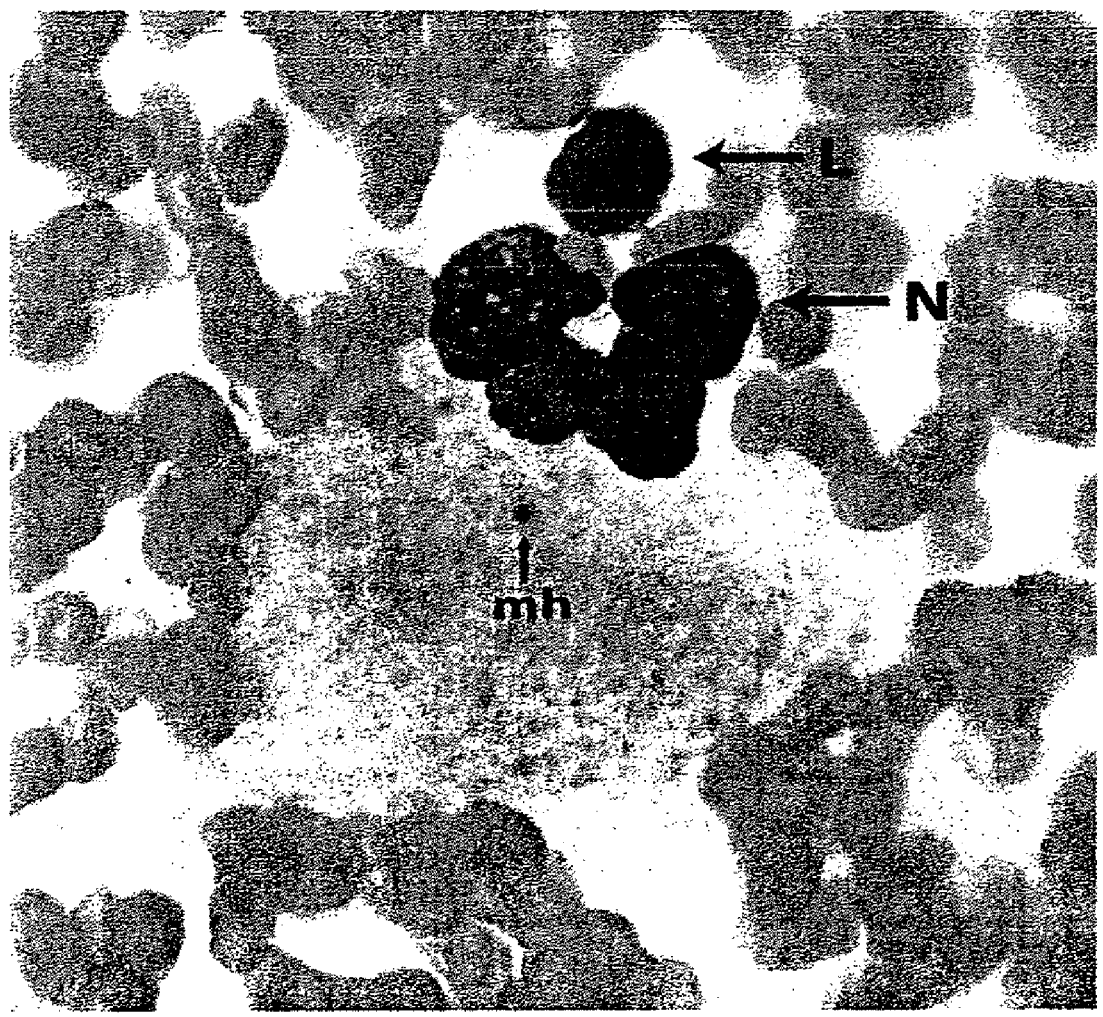
FIG. 4 is a photomicrograph of a megakaryocyte from another SLE patient. The arrow adjacent to "mh" indicates an inclusion morphologically similar to the *mycoplasmas* seen in FIGS. 1-3. The arrow adjacent to "L" indicates a lymphocyte, whereas the arrow adjacent to the "N" indicates a nucleus.

One way to assess how long to continue administration of an above-noted drug is to continue administration until the stainable, phase contrast microscopically visible, exogenous bacterial structures seen in SLE patient's megakaryocytes (e.g., as in FIG. 4) prior to treatment are absent from the megakaryocytes, and preferably until no further evidence of infection is present. This duration of administration can take as long as about 120 days, the average lifetime of an erythrocyte, or more. Periodically repeated administrations of drugs that encompass the average lifetime of an erythrocyte are thus contemplated and are preferred.

A contemplated composition can be a solid or a liquid. The active ingredients can also be individually admixed as a suspension of solids in a solid or liquid physiologically tolerable carrier, or dissolved as a solute or suspended in the carrier, or a combination thereof.

Physiologically tolerable carriers are well known in the art. Exemplary of liquid carriers are sterile aqueous solutions that can contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose and other solutes. These latter carriers are exemplified by Ringer's Injection, Dextrose Injection, Dextrose and sodium chloride Injection and Lactated Ringer's Injection.

Liquid compositions can also contain liquid phases in addition to and to the exclusion of water. Exemplary of such additional liquid phases are glycerin, vegetable oils such as sesame oil or cottonseed oil, and water-oil emulsions.

Exemplary solid carriers include those materials usually used in the manufacture of pills or tablets, and include corn starch, lactose, dicalcium phosphate, thickeners such as tragacanth and methylcellulose U.S.P., finely divided $SiO_2$, polyvinylpyrrolidone, magnesium stearate and the like. Additionally, the solid carrier can include biodegradable and non-biodegradable polymers, polypeptide carriers, affinity carriers such as AFFI-GEL® 601 (phenyl boronate resin available from Bio-Rad Laboratories, Richmond, Calif.), liposomes and synthetic polymers, as are known in the art. Antioxidants such as methylparaben and propylparaben can be present in both solid and liquid compositions, as can sweeteners such as cane or beet sugar, sodium saccharin, sodium cyclamate and the dipeptide methyl ester sweetener sold under the trademark NUTRASWEET® (aspartame) by Merisant Corporation.

It is particularly preferred, however, to utilize the orally administratable tablet and capsule forms of a before-mentioned pharmaceutical product.

EXAMPLES

The following examples are presented to illustrate certain aspects of the invention and are not intended to limit the scope of the invention.

Human Patients

Patient A

Patient A, a 36-year-old African-American female was hospitalized in May 1988 for treatment of idiopathic thrombocytopenic purpura, caused by presumed hypersplenism. She underwent splenectomy and within three years had developed the multiple laboratory and clinical abnormalities that were defining of SLE. These abnormalities consisted in part of elevated anti-dsDNA, arthritis, cutaneous lesions consistent with *lupus*, and lupus nephritis. When examined in 1994, her erythrocytes had intra-erythrocytic inclusions occupying 16% of the counted erythrocytes. These Giemsa-stained particles were about 0.5 µ in diameter, inside the erythrocyte in the marginal position, and did not appear to cause changes in the erythrocytic structure. By bright field light microscopy they had no internal structure, and, because they appeared to be contained within a vacuole, were different in appearance from Howell-Jolly bodies when visualized by phase microscopy.

A trial of doxycycline 100 mg twice daily was instituted, based on known activity against erythrocyte-associated-organisms erythrocyte-associated organisms in related erythrocyte animal infections such as bovine anaplasmosis [Wanduragala et al., "Anaplasmosis" in *Rickettsial and Chamydial Diseases of Domestic Animals*, Woldehiwet et al. eds., Oxford, Pergamon Press, Chapter 3, 69-88 (1993)]. This treatment was followed with treatment by clarithromycin 250 mg q 12 hours, and rifampicin 600 mg daily. During the period of antibiotic treatment in 1996, she was evaluated monthly with counts of erythrocyte parasitization, studies of anti dsDNA, and general medical physical examination including evaluation of her oral and cutaneous lesions.

Patient B

Patient B was a Caucasian female born in 1976, had never left Norway, and first had thrombocytopenia at age 14. She underwent splenectomy at age 15 and following this procedure, over the next two years, experienced a cascade of thrombocytosis, butterfly malar rash, a positive anti-nuclear antibodies (ANA), and arthralgia. A kidney biopsy was consistent with lupus nephritis. These findings were consistent with the diagnosis of SLE. She subsequently suffered several episodes of thromboembolic disease, which resulted in loss of the left leg, left cerebral stroke with right hemi-paresis, and an intracardiac thrombus by age 19. FOollowing discovery of intra-erythrocytic structures, she was treated with doxycycline 100 mg twice daily, and following this, with clarithromycin 250 mg q 12 hours, and rifampicin 600 mg daily. All antibiotics were discontinued by her medical attendants after the thrombus to her leg. She suffered a myocardial infarction at age 21.

Her peripheral blood smear was examined on three occasions in 1995, and twice in 2003. The percentage of erythrocytes with inclusions observed optically was as follows: 1995, 0.5%; 2003, 3.8% and 0.6% six months later.

Determination of Percentage of Affected Erythrocytes

Blood smears collected for examination were spread as thin smears on pre-cleaned glass microscope slides and fixed in absolute methanol. On an optical projection of appropriate stained thin sectors of blood with observations only of erythrocytes, a count is taken of all the erythrocytes seen within the borders of the optical projection with the infected erythrocytes noted, counted, and the result calculated and expressed as the percent parasitized erythrocytes.

Blood Studies

For use in whole blood electron microscopy, heparinized blood was washed with 20× volumes of PBS pH 7.4, and centrifuged. Cells in the resulting pellet were resuspended in freshly prepared paraformaldehyde and 1% glutaraldehyde in 0.1 M sodium cacodylate buffer pH 7.4. The initial fixation was carried out at 4° C. for one hour. Fixed cells were then washed twice in 0.1 M cacodylate buffer and resuspended in 2% low temperature gelling agar. Then, 1-1.5 mm diameter ribbons of agarose containing fixed cells were fixed in the original fixative for two hours at 4° C. Ribbons were washed several times and post fixed with 2% osmium tetroxide in cacodylate buffer for one hour on ice. Finally, these fixed ribbons were washed several times with water, dehydrated with successively increasing concentrations of alcohol, immersed in two changes of propylene oxide, then immersed in propylene oxide/Spurr's resin (1:1 mix) overnight prior to embedding in Spurr's resin and polymerization of blocs in 60° C. oven.

In other blood studies, blood smears were prepared on clean glass slides, air-dried and fixed in methanol for 2 minutes. Stock Giemsa stain was diluted 1:10 with buffer solution. The working stain solution was filtered through a 0.2 micron pore filter, and overlaid directly on the smear for one hour.

Slides were examined at 500× and 1000× magnification. When a representative intra-erythrocytic structure was seen with transmitted bright field illumination, the optics were changed to phase contrast, without moving the slide. The blue gray erythrocytic inclusions were interpreted as enclosed win a vacuole.

In appropriately spread areas of Giemsa-stained peripheral blood smears, all erythrocytes and infected erythrocytes were counted. The percentage of infected erythrocytes was calculated.

In examinations for mitochondria, blood smears were subjected to staining and fluorescent spectroscopy. The thin blood smears were fixed in absolute methanol, overlaid with MitoTracker® (MitoTracker® Green FM, Invitrogen, Carlsbad, Calif.) and examined by epifluorescent microscopy. When a fluorescent intra-erythrocytic structure was found, the optics were switched to phase contrast to further determine if the structure were coincident with another inclusion.

Examination of Archived Bone Marrow Specimens

Twenty specimens of bone marrow, taken from archives at Rush University Medical Center, were numbered. These specimens included bone marrow specimens from 14 patients with SLE and 20 patients without that diagnosis. This information had been extracted from their record by a third party and was kept confidential to blind the specimens to the investigators.

The blinded specimens were examined by two investigators at 500 to 1000 ×, with particular attention to the megakaryocytes (MGKC) with at least 20 megakaryocytes visualized. If intercalating-dyable intra-megakaryocytic inclusions were seen, the marrow was declared to be positive. If fewer than 20 MGKC were seen, the specimen was not included in the results. If too much stain precipitate was present, the specimen was not counted. When the code was broken, the identifying number was removed, and replaced by a study designation, so that the identity of any patient was not present in any interpretation.

DNA Handling

Dnazol® (Molecular Research Center, Inc., Cincinnati, Ohio) was utilized for genomic DNA isolation from 0.5 ml of whole blood of both healthy control subjects and *lupus* patients.

The AccuPrime™ polymerase chain reaction (PCR) system available from Invitrogen was selected for routine use. Forward and reverse primers and bacterial primers were selected from those known to polymerize bacterial DNA in general and *mycoplasmas* specifically. Forward and reverse primers were designed at Michigan State University (MSU) and were synthesized by the MSU Macromolecular Facility, near positions 949 and 1404 (*E. coil* numbering), respectively. Forward and reverse primers were selected for the known *Mycoplasmas, M. haemosuis, M. haemofelis, M. haemocanis* and *M. Haemomuris*, more usually *Haemobartonella muris*.

Results of Antibiotic Treatment—General

Clinical parameters of objective and subjective disease of both *lupus* patients A and B improved with both doxycycline and clarithromycin and rifampicin, though the improvement of subjective symptoms seemed greater with the latter combination to the patients as well as the investigators. Both patients had changes in their erythrocytes following clarithromycin and rifampin that suggested bacterial disintegration and disappearance of bacterial substance within the vacuoles. Multiple vacuoles post bactericidal antibiotics were also seen without phase illumination suggesting emptying of the contents of the vacuoles. These empty vacuoles seen under bright field illumination were not present in either patient or any other patient's blood examined before the antibiotic therapy though all specimens were collected and treated in the same way.

Results of Antibiotic Therapy

Patient A

Upon institution of therapy with doxycycline, the percentage of parasitized erythrocytes began a decline over several months. This decline appeared to be logarithmic, and was confirmed by a graph of the logs of the percentage of parasitized erythrocytes, which was linear. This decline was accompanied with clinical improvement in skin lesions and oral ulcerations as well as a decline in anti dsDNA levels after treatment with Doxycycline for 6 months. However, by bright field microscopy in Giemsa-stained blood films, there were still intra-erythrocytic inclusions that were enclosed in a vacuole, suggesting that although significant clinical improvement occurred as well as a decline in anti-dsDNA, and a decline in intra-erythrocytic bodies, it appeared that doxycycline had not completely eliminated the inclusions.

The second antibiotic course of clarithromycin and rifampicin caused a fundamental change in the inclusions. Within several weeks, the intra-erythrocytic structures became fragmented and disappeared from the vacuoles in the erythrocytes. The vacuoles could now be seen without phase contrast optics and continued clinical improvement occurred. The cutaneous lesions on the neck and face continued their resolution, and the oral lesions disappeared. The patient returned to treatment by a rheumatologist and was lost to follow-up.

Patient B

Reports of the patient condition suggested marked clinical improvement with antibiotic therapy, and after the treatment with clarithromycin plus rifampicin was begun, similar changes in the intra-vacuolar bodies to those seen in patient A occurred, with fragmentation and the appearance of empty vacuoles in the erythrocyte following the bactericidal antibiotics. All antibiotics were discontinued by the treating physician following severe thromboembolic events coincident with extremely high platelet counts. Her peripheral blood smear was examined on three occasions: once in 1995 and twice in 2003. The empty vacuoles seen under bright field illumination were not seen in any other patients, although all specimens were treated in the same way.

Observations of Giemsa-Stained Blood Films of Splenectomized Lupus Patients

Seven splenectomized *lupus* patients were studied, including patients A and B. All upon careful examination had 0.3-0.5 micron in diameter intra-erythrocytic bodies, which upon phase contrast optics appeared to be within a vacuole. With use of MitoTracker® and phase contrast microscopy, showed the intra-vacuole structures to be different from mitochondria. No percentage of erythrocytes with inclusions exceeded 1%, within parameters permitted by sampling error. The two splenectomized index patients had from about 4% (Patient B) to about 16% (Patient A) of the observed erythrocytes parasitized.

Blood from Patient B was observed in 1995 before antibiotic treatment and less than 1% of the erythrocytes exhibited inclusions. When her blood was examined in 2003, and she was under no antibiotic treatment, the count was about 4%. The DNA extracted from this specimen led to the determination of a mycoplasmal 16 S rRNA by PCR. Six months later, the percentage of infected erythrocytes had returned to less than 1%.

Results of Polymerase Chain Reaction (PCR)

Multiple PCR studies were carried out using non-splenectomized *lupus* patients using nested PCR procedures. The results of controls and patients were not different. Multiple amplicons were obtained. Most identification of bacterial DNA appeared to agree with the previously reported presence of bacterial DNA found in normal blood. [Nikari et al., *J. Clin. Microbiology*, 39:1956-1959 (2001); and Vernon et al., *Microbiology*, 2:39 (2003).] Patient B, who at the time of examination in 2003 had about 4% of her erythrocytes parasitized with Giemsa-positive structures within a vacuole, repeatedly and reproducibly yielded an amplicon of 417 bp 16 S rRNA from DNA of the single available previously frozen whole blood specimen, which was identified as within 1% DNA homology of the two hemotropic *mycoplasmas*, known as *M. haemocanis* and *M. haemofelis*. [Tasker et al., *J. Clin. Microbiology*, 41:3877-3889 (2003).]

Electron Microscopy of Contents of an Intra-Erythroctic Vacuole in Patient A

Intra-erythrocytic vacuoles tended to be oval in shape, and were often paired with one or more bacteria-like structures within one or both of the paired structures. A single vacuole was closely examined. The bacteria like structure was 0.5 micron in diameter, and was enclosed within a vacuole that was similar in appearance to the erythrocyte limiting membrane. Observable internal features included two well-defined structures that resembled tangential sections of a helical cytoskeleton. There was no rigid cell wall. Multiple observations of this fixed block of blood, sampled at approximately 8% parasitemia, confirmed that the structures seen were repeatedly observed, and confirmed the level of parasitemia observed with light microscopy when the blood was originally drawn. This blood sample was taken during the course of therapy with doxycycline, and the percentage had declined from about 16% to about 8%. The structures were consistent with a member of the *Mollicutes*, because members of the *Mollicutes*, *Spiroplasma*, *Acholeplasma*, and *Mycoplasma*, exhibit a cytoskeletal structure. [Razin et al., *Microbiology and Microbiological Reviews*, 62:108-2172 (1992).] The intra-bacterial structures were different from mitochondrial cristae, which are contiguous with the cell membrane.

Microscopic Examiniation of Archived Bone Marrow Specimens

A search of megakaryocytes in *lupus* marrow specimens was conducted after marrow of a patient with SLE and persistent leucopenia was examined, and an inclusion identified. See, FIG. 4.

A series of marrow aspirate slides was examined with the identity of the patient's disease being blinded to the examiner. After the codes were broken, fourteen specimens were found to have been evaluated from patients with a diagnosis of SLE: 11 of 14 of those patients had inclusions in their megakaryocytes consistent with small bacterial structures as seen by Giemsa-based stain. Of twenty patients with preliminary diagnoses other than *lupus*, nine had inclusions consistent with the described intra-megakaryocytic structures identified by morphology of small inclusions near the limits of optical resolution, and complicated by granules from disrupted cells in marrow aspirates.

On re-examination of marrow slides by the investigators, the proportion of *lupus* marrows with megakaryocytic inclusions remained significantly higher than "controls", but the concordance of results on specific specimens was not exact. It was concluded that differences in results from various readings of the still blinded specimens were attributable to an attempt to identify morphology of small inclusions near the limits of the optical resolution, and complicated by granules from disrupted cells in marrow aspirates.

Each of the patents and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

What is claimed:

1. A method for diagnosing systemic lupus erythematosus which comprises detecting bacterial structures within megakaryocytes of a patient.

2. The method of claim 1 wherein the detecting is done by staining the megakaryocytes with a dye and visualizing bacterial structures within the megakaryocytes.

3. The method of claim 1 wherein the dye is a DNA intercalating dye.

4. The method of claim 1 wherein the dye is Giemsa, ethidium bromide or acridine orange.

5. A method for diagnosing systemic lupus erythematosus which comprises staining megakaryocytes with a DNA intercalating dye and visualizing by phase contrast microscopy bacterial structures within the megakaryocytes.

6. A process for treating a patient whose megakaryocytes contain bacterial structures, the process comprising (a) detecting bacterial structures within megakaryocytes of a patient and (b) administering to said patient an antibacterial agent that is (i) an antibacterial amount of a rifamycin along with an antibacterial amount of a macrolide, (ii) an antibacterial amount of a tetracycline, or (iii) an antibacterial amount of a quinolone, or a mixture of two or more of i, ii, and iii.

7. The process according to claim 6 wherein the antibiotic mixture comprises a rifamycin and clarithromycin or doxycycline.

8. The process according to claim 6 wherein the antibiotic agent (i) a macrolide that is selected from the group consisting of erythromycin, clarithromycin, erythromycin 2'-acetate octadecanoate, erythromycin estolate, dirithromycin, azithromycin, celithromycin and spiramycin along with a rifamycin that is rifampin, rifabutin or rifamide, (ii) a tetracycline that is selected from the group consisting of tigacycline, doxacycline or minacycline, (iii) a quinolone compound that is selected from the group consisting of nalidixic acid, ciprofloxacin, levofloxacin, moxifloxacin, gatifloxacin, tefloxacin and trovafloxacin, or a mixture of one or more of i, ii and iii.

9. The process according to claim 6 wherein said rifamycin is rifampin or rifabutin.

10. The process according to claim 6 wherein said administrations are per oral.

11. The process according to claim 6 wherein said administrations are repeated periodically until said bacterial structures are eliminated from the patient's megakaryocytes.

12. The process according to claim 6 wherein the amount of doxycycline administered is about 100 mg twice daily, the amount of clarithromycin administered is about 250 mg every 12 hours, and the amount of rifampicin administered is about 600 mg daily.

13. The process according to claim 6 including the further step of assaying a patient's megakaryocytes for the presence of bacterial structures there within.

* * * * *